United States Patent [19]

Helzel

[11] Patent Number: 4,646,086
[45] Date of Patent: Feb. 24, 1987

[54] ARRANGEMENT FOR DATA TRANSMISSION BETWEEN TWO MUTUALLY ROTATABLE PARTS

[75] Inventor: Thomas Helzel, Hamburg, Fed. Rep. of Germany

[73] Assignee: U.S. Philips Corporation, New York, N.Y.

[21] Appl. No.: 688,100

[22] Filed: Dec. 31, 1984

[30] Foreign Application Priority Data

Jan. 7, 1984 [DE] Fed. Rep. of Germany ....... 3400361

[51] Int. Cl.⁴ .............................................. G08B 1/00
[52] U.S. Cl. ............................. 340/870.29; 340/347 P
[58] Field of Search .......... 340/870.29, 347 P, 870.28, 340/870.41; 250/231 SE; 318/640; 33/1 PT; 350/485

[56] References Cited

U.S. PATENT DOCUMENTS 3,493,959 2/1970 Cap .................................. 340/347 P
4,175,230 11/1979 Richards et al. ........... 340/870.28 X Primary Examiner—Jerry W. Myracle
Attorney, Agent, or Firm—Jack E. Haken

[57] ABSTRACT

The invention relates to an arrangement for data transmission between two mutually rotatable parts, in particular for computer tomographs, in which the signal can travel along two separate paths from transmitter to receiver, so that the phase angle and amplitude, respectively, of the received signal changes upon one rotation. For the signals propagating along the two distinct paths a separate receiving channel is provided for each path with a limiter amplifier, the output signals of the limiter amplifier being fed to inputs of an OR circuit whose output signal forms the output signal of the data transmission network.

3 Claims, 5 Drawing Figures

ARRANGEMENT FOR DATA TRANSMISSION BETWEEN TWO MUTUALLY ROTATABLE PARTS

The invention relates to an arrangement for data transmission between two mutually rotatable parts, one of which carries a transmitting arrangement and the other a recieving arrangement, where the receiving arrangement comprises at least two photodiode transducers which receive signals whose phase angle and/or amplitudes change in opposite directions upon rotation of the parts.

Figure 1:
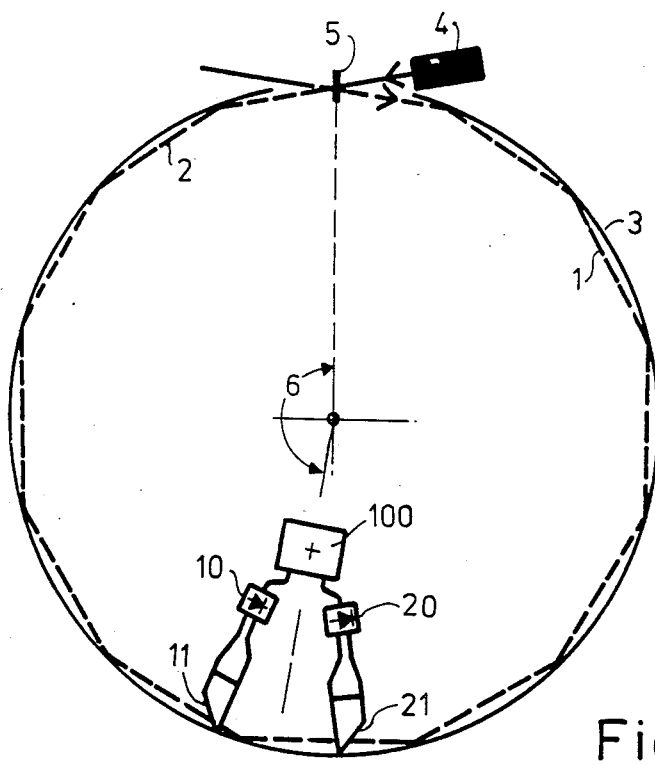

An arrangement of this type is known from DE-OS No. 32 05 065 and is illustrated in FIG. 1. The known arrangement comprises an internally reflecting concave cylindrical mirror 3, with which a transmitting arrangement in the form of a laser 4 is rigidly connected. A part inside the mirror 3, not described in detail, carries a receiving arrangement consisting of two reception transducers (photodiodes) 10 and 20. The mirror 3 and the parts carrying the receiving arrangement are rotatable relative to one another.

The laser 4 transmits a parallel beam of rays which, by means of a beam splitter 5 in the form of a mirror, is split into two beams parallel to the plane of the drawing in FIG. 1, which beams, having the same intensity but rotating in opposite directions and in planes perpendicular to the plane of the drawing in FIG. 1 are reflected from the inside face of the mirror 3. This division into two beams of rays is necessary because the bit rate (each bit being characterized by a high or a low intensity of the laser light) is so high that otherwise, upon rotation of the parts, travel time discontinuities would take place that would make evaluation of the signal impossible. In the planes in which the beams 1 and 2 rotate about one half of the inside surface of the concave cylinder 3 is alternately non-reflecting, resulting approximately in the following behaviour:

As long as the angle 6, shown in FIG. 1, between the beam splitter 5 and the center of the receiving arrangement is substantially smaller than 180° the beam 2 is led via the mirror 21 to the photodiode 20. At this angle the photodiode 10 receives no signal, because the beam 1, before it can reach the mirror 11 allocated to the photodiode 10, strikes the non-reflecting part of the inside surface, where it is absorbed. If the angle 6 is made substantially larger than 180°, the situation is reversed. The beam is then led to the photodiode 10, while the photodiode 20 receives no light. When the arrnagement 10, 20 is diametrically opposite to the mirror 5 (the angle 6 is then precisely 180°) and moves in a particular angular range (e.g. 2°) around this angular position, both photodiodes 10, 20 receive the allocated beams 1 and 2.

For further evaluation the two photodiodes in the known arrangement are connected in parallel (see page 4, paragraph 2 of DE-OS No. 32 05 065), i.e. the currents of the photodiodes are added by an adder circuit 100. By virtue of this addition the noise level associated with the two signals is also added, even when one of the photodiodes cannot be struck by the allocated beam, as a result of which the input sensitivity of the evaluating circuit is reduced.

The purpose of the invention is to generate from the output signals of the photodiodes, without any such reduction of the input sensitivity, a signal that will largely correspond to the signal of the transmitting arrangement.

This purpose is achieved by the invention in such a way that the photodiodes are each followed by a limiter amplifier whose output signals are fed to the inputs of an OR circuit whose output signal forms the output signal of the receiving arrangement.

Through the limiter-amplifier all instantaneous values of the signal that lie above a particular threshold value receive a first level and all instantaneous values lying thereunder receive a second level, so that the signal, upon exceeding the threshold value, is converted into an essentially binary signal which is further processed by the OR circuit. The noise level present in the two channels is not thereby added.

Figure 2:
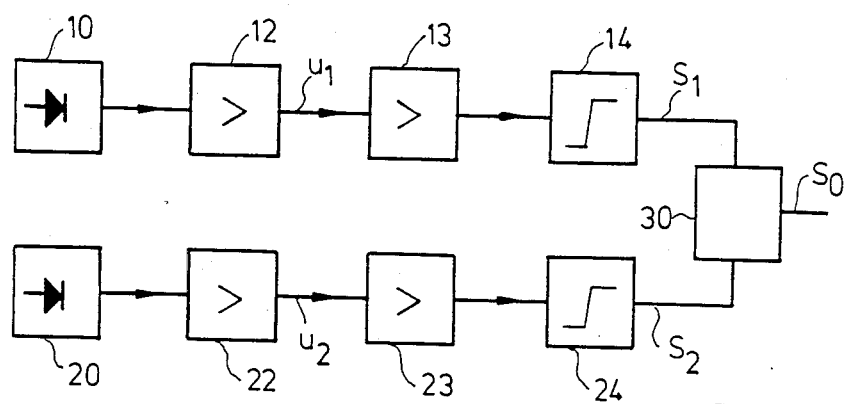
Figure 4:
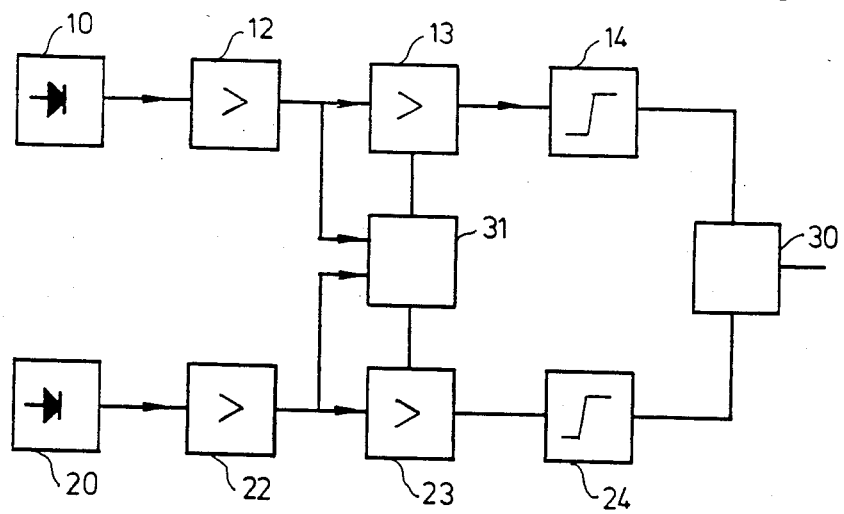
Figure 3:
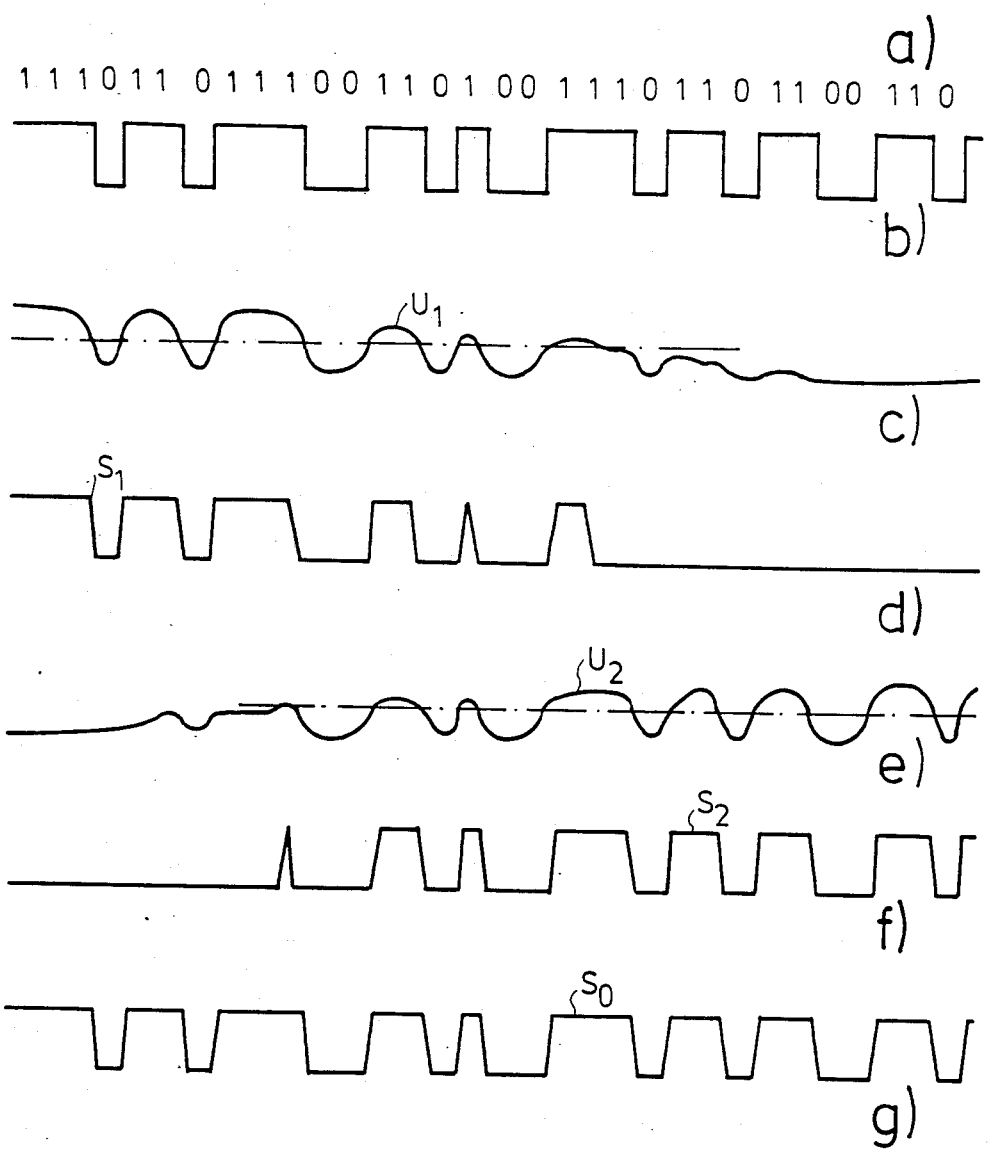

The invention will be elucidated below with reference to the appended drawings, in which FIG. 1 shows the known arrangement for data transmission, in which the invention is also applicable, FIG. 2 shows a first embodiment of the invention, FIG. 3 shows the waveform of the signals in the various channels and at the output of the OR circuit, FIG. 4 shows a further embodiment.

Figure 5:
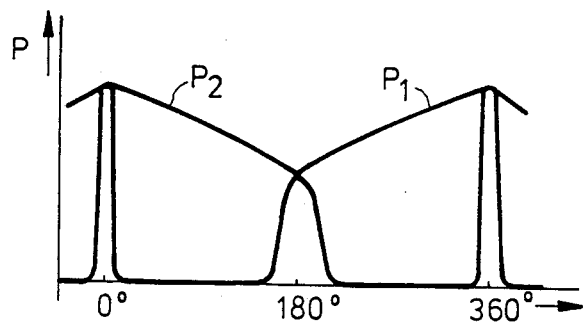

FIG. 5 shows the signal level in the two channels as a function of the angle of rotation 6, The signals delivered by the two reception transducers, the photodiodes 10 and 20, which, like the transmitter, are in an arrangement as shown in FIG. 1, are each fed to a pre-amplifier 12 and 22 respectively (FIG. 2). The output signals $u_1$ and $u_2$ from the preamplifiers 12 and 22, respectively, are fed to radio-frequency amplifiers 13 and 23, respectively, which are in the form either of a controlled (broad-band) dc amplifier or of an ac amplifier. The output signals of the respective RF amplifiers 13 and 23 are fed to limiter-amplifiers 14 and 24, respectively. The output signals $s_1$ and $s_2$ of the limiter-amplifiers 14 and 24 are fed to the inputs of an OR circuit 30, whose output signal $s_0$ has essentially the same waveform as the intensity of the laser beam 4. The information to be transmitted by the data transmission arrangement is illustrated in FIG. 3a. This information consists of a sequence of "1" and "0". The bit rate is about 150 Mbits/s when the data transmission arrangement is used with a computer tomograph.

The information as in FIG. 3a modulates the intensity of the laser in such a way that the beams 1, 2 emitted by the laser have a high intensity for a "1" and a very low or zero intensity for an "0". The waveform of the intensity of the beams 1, 2 is illustrated in FIG. 3b.

One of the two beams 1, 2 reaches the allocated photodiodes 10 or 20; when the angle between the beam splitter 5 and the receiving arrangement 10, 20 is 180°, both beams reach the corresponding photodiodes. The transit time and amplitude depend in this connection on the angle 6. For the purposes of computer tomography the diameter of the mirror 3 is about 1 m, so that the transit time of the laser beams 1, 2 from the beam splitter 5 to the position on the cylindrical mirror 3 diametrically opposite to it is in the order of magnitude of the rate at which the individual information bits follow one another.

The electrical signals generated by the photodiodes 10, 20 acting as transducers in the reception of the beams 1 and 2 are very weak (of the order of $\mu A$) and their waveform relative to the waveform of the light intensity at the output of the laser (FIG. 3d) is severely deformed. The amplifiers 12 and 13 or 22 and 23, as the case may be, linearly amplify the output signal of the photodiodes 10, 20, so that the signals at the outputs of 10, 12 and 13 on the one hand and at 20, 22 and 23 on the other hand each show the same temporal waveform but not the same amplitude. The respective signals $u_1$ and $u_2$ in the channels are shown in FIG. 3c and 3e. It can be seen that the amplitude of the signal $u_1$ decreases while the amplitude of the signal $u_2$ increases, because the part carrying the receiving arrangement 10, 20 and the cylindrical mirror 30 are mutually rotated (with a revolution per second) in such a way that the angle 6 (FIG. 1) decreases.

It can further be seen that in a particular temporal (overlapping) range neither of the two signals disappears. Before and beyond this range only one of the two signals $u_1$ and $u_2$ differs from zero, because the receiving arrangement 10, 20 than takes up an angular attitude in which only one of the two beams 1, 2 reaches the allocated photodiode, whereas the other beam, as already mentioned, is largely absorbed by the non-reflecting area of the cylindrical mirror 3. In the drawing this area is only a few bit periods long; in reality however, it amounts to some one million bit periods when it is assumed that, upon a rotation with one revolution per second during about 6 msec. (corresponding to an angle overlapping range of about 2°) both photodiodes receive a signal differing from zero. In the invention a smooth transition is thereby effected from one channel to the other.

In FIG. 3c and FIG. 3e the threshold values of the limiter-amplifiers 14, 24 are given as dot-dash lines. When the voltage $u_1$, $u_2$ (after amplification by the amplifiers 13, 23) are above this threshold value, the output signal of the limiter-amplifiers 14 and 24, respectively, takes on a first value and when the signal lies below the said threshold value it takes on a second value. The signals $s_1$ and $s_2$ thus generated are shown in FIGS. 3d and 3f. It can be seen that the two first positive pulses of the signal as in FIG. 3b are contained only in the output signal $s_1$ of the limiter-amplifier 14. Upon the next pulse the limiter-amplifier 24 is indeed actuated but only very briefly, because the signal $u_2$ reaches the threshold value only for a short time. This pulse is substantially shorter than the third pulse of the laser (FIG. 3b), which is nevertheless very well approximated by the third pulse of the signal $s_1$, the waveform of the output signal $s_0$ of the OR circuit corresponds at this point of time in practice to the signal $s_1$, that is to say the weaker signal (in this case $s_2$) is suppressed. In the further course the amplitude of $u_1$ decreases and the amplitude of $u_2$ increases to such an extent that $u_2$ becomes greater than $u_1$. The waveform of the signal b is then represented better by $s_2$ than by $s_1$ and the output signal $s_0$ is determined by the corresponding pulse in the signal $s_2$. In this way a gradual transition takes place from one channel (10, 12, 13, 14) to the other channel (20, 22, 23, 24), the output signal of the OR circuit $s_0$ thereby being determined in each case by those parts of the signals $s_1$, $s_2$ that better corresponds to the waveform of the original signal (FIG. 3b).

FIG. 4 shows an embodiment in which the amplification in the two channels is switched over, in dependence on the signal level, in such a way that the amplification is always greater in that channel that has the higher signal level. In this connection reference may be made to FIG. 5, which shows the optical power $P_1$, $P_2$ at the location of the photodiodes 10 and 20 as a function of the angle 6. The optical power $P_2$ at the input of the photodiode 20 has a maximum at 0°, because the beam 2 at this point has reached the photodiode 20 virtually unattenuated. With increasing angle of rotation the intensity $P_2$ decreases, because the beam 2 is reflected and loses in intensity. When the angle 6 becomes somewhat larger than 180°, a marked decrease in power occurs because the beam 2 on its way to the photodiode 20 strikes areas that show zero or very little reflection, until, upon further increasing angle of rotation 6, the power reaches the value $P_0$. The optical power received by the photodiode 10 shows precisely the opposite course as a function of the angle of rotation 6, that is to say symmetrical with the normal at 180°. At angles that are slightly greater than 0 up to angles that are slightly less than 180° virtually no light reaches the photodiode 10. Thereafter, the optical power rises with the angle of rotation—strongly up to 180° and subsequently less—until it reaches a maximum at 360°. In this way the optical powers received by the photodiodes 10 and 20, or the ratio of these powers, can be used as a measure of the angular position in order, in the range of 180°, to achieve a transition from one channel to the other channel. In principle this could also be done with the aid of an angle transducer but this would involve additional outlay.

Since the time average of the signals $u_1$, $u_2$ (averaged over a short time compared with a full revolution between transmitting arrangement 4 and receiving arrangement 10, 20) corresponds to the optical power $P_1$, $P_2$, the signal $u_1$, $u_2$ can also be used for driving the amplifier. For this purpose these signals are fed from the output of the preamplifier 12 or 22 via a time-constant member, not further specified, to the inputs of a window comparator 31 which is coupled with the driving inputs of the radio-frequency amplifiers 13 and 23, in such a way that both radio-frequency amplifiers show the same sensitivity when the level difference between the two input signals falls below a prescribed value (e.g. 5 dB) and in the other case a reduction takes place in the sensitivity of that RF amplifier 13 or 23 to which the signal with the lower level is fed. The change in sensitivity can take the form of a change in amplification or a shift in the operating point (trigger level).

The window comparator can be built up from two comparators, to one of which one of the two signals $u_1$ and $u_2$ is fed directly while the other ($u_2$ or $u_1$) is fed via an attenuator, whose attenuation is equal to the required level difference (5 dB) and whose outputs are connected with the drive outputs of the radio frequency amplifiers 13 and 23, respectively. The output signal of the high frequency amplifiers 13 and 23, whose sensitivity is controllable, is again transformed by respective limiter-amplifiers 14 and 24 and fed to the two inputs of the OR circuit 30, so that the circuit in FIG. 4 differs from the circuit in FIG. 2 only in the window comparator 31 in as much as the radio frequency amplifiers 13 and 23 show a sensitivity which is controlled by a signal at their drive inputs. Because of this modification, interfering signals in the channel not being used for data transmission are suppressed even when their amplitude lies in the order of magnitude of the normal level signal.

Although the invention has been elucidated with reference to a data transmission arrangement in accordance with DE-OS No. 32 05 605, it is also applicable to other arrangements for data transmission between two mutually rotatable parts in which the phase position (transit time) and/or the amplitude of the received signal changes upon a rotation between the parts. An example of this is to be found in DE-OS No. 33 31 722, when a second receiver-coupling element is used arranged in such a way that it is opposite to the middle between two neighbouring transmitter-coupling elements when the other receiver-coupling element is exactly opposite to a transmitter-coupling element. In that case the amplitude received from the one coupling element is maximum while the signal amplitude received from the other coupling element is minimum, and here too, it is possible, in the manner described in the foregoing, to effect a transition from one channel to the other channel such that the data transmission is always determined by that channel that has the strongest signal at any given time.

What is claimed is:

1. An arrangement for data transmission between two mutually rotatable parts, one of which carries transmitting arrangement (4) and the other receiving arrangement, where the receiving arrangement comprises at least two photodiode transducers (10, 20) which receive signals whose phase angle and/or amplitudes changes in opposite directions upon rotation of the parts, in which the reception transducers (10, 20) are each followed by a limiter-amplifier (14, 24) whose output signals are fed to the inputs of an OR circuit (30) whose output signal ($s_o$) forms the output signal of the receiving arrangement.

2. Arrangement as claimed in claim 1, in which, for driving the amplifiers in the channels from the output of the photodiode transducers to the inputs of the OR circuit, a circuit is provided which, up on equality in the amplitudes and/or phases, increases and/or decreases the sensitivity in the other channel.

3. Arrangement as claimed in claim 1, in which the circuit contains a comparator which compares the levels of the signals ($u_1$, $u_2$) delivered by the photodiode transducers (10, 20) and drives the amplifiers of the two channels in such a way that the amplification in the channel with the lower level is smaller than in the channel with the higher level.

* * * * *

UNITED STATES PATENT AND TRADEMARK OFFICE
CERTIFICATE OF CORRECTION

PATENT NO. : 4,646,086
DATED : February 24, 1987
INVENTOR(S) : THOMAS HELZEL

It is certified that error appears in the above-identified patent and that said Letters Patent is hereby corrected as shown below:

IN THE ABSTRACT:

Line 1, "The invention relates to an" should be
--An--.

Column 4, line 21, delete "but this would involve".
line 22, delete "additional outlay".

Claim 1, line 3, "arrangement" should be --means--.
"arrange-" should be --means--.

line 4, delete "ment"; "where" should be
--wherein--; "arrangement" should be
--means--.

line 6, "angle" should be --angles--.

line 7, "reception" should be --photodiode--.

Claim 2, line 1, "Arrangement as" should be --The
arrangement--; "in which" should be
--further comprising circuit means which
functionally connect--.

line 2, delete "driving"; "amplifiers" should be
--limiter-amplifiers--; insert --each of--
after "in".

line 3, "transducers" should be --transducer--;
"the inputs" should be --an input--.

UNITED STATES PATENT AND TRADEMARK OFFICE
CERTIFICATE OF CORRECTION

PATENT NO. : 4,646,086
DATED : February 24, 1987
INVENTOR(S) : THOMAS HELZEL

It is certified that error appears in the above-identified patent and that said Letters Patent is hereby corrected as shown below:

Claim 2, line 4, "a circuit is provided" should be --and--.
         line 5, delete "increases and/or de-".
         line 6, "creases" should be --increase and/or decrease--.

Claim 3, line 1, "Arrangement as" should be --The arrangement.
         line 2, "circuit contains" should be --receiving means contain--.
         line 4, "amplifiers" should be --limiter-amplifiers--.
         line 6, insert --the amplification-- after "than".

Signed and Sealed this

Sixth Day of October, 1987

Attest:

DONALD J. QUIGG

Attesting Officer      Commissioner of Patents and Trademarks